(12) United States Patent
Lifran et al.

(10) Patent No.: US 7,754,876 B2
(45) Date of Patent: Jul. 13, 2010

(54) METHOD FOR PURIFICATION OF LACTOSE

(75) Inventors: Estelle V. Lifran, Epping (AU); Robert W. Sleigh, Rose Bay (AU); Robert L. Johnson, Castle Hill (AU); Robert J. Steele, Vaucluse (AU); James A. Hourigan, Castle Hill (AU); Sean M. Dalziel, Wilmington, DE (US)

(73) Assignee: Dairy Australia Limited, Southbank (AU)

( * ) Notice: Subject to any disclaimer, the term of this patent is extended or adjusted under 35 U.S.C. 154(b) by 0 days.

(21) Appl. No.: 10/451,347

(22) PCT Filed: Dec. 19, 2001

(86) PCT No.: PCT/AU01/01641

§ 371 (c)(1), (2), (4) Date: Feb. 6, 2004

(87) PCT Pub. No.: WO02/50089

PCT Pub. Date: Jun. 27, 2002

(65) Prior Publication Data

US 2004/0132989 A1    Jul. 8, 2004

(30) Foreign Application Priority Data

Dec. 19, 2000   (AU)   ................... PR 2177

(51) Int. Cl.
*C13K 5/00*   (2006.01)
*C07H 3/04*   (2006.01)

(52) U.S. Cl. .................. 536/123.13; 536/124; 536/127; 514/53

(58) Field of Classification Search ............ 536/123.13, 536/124, 127; 514/53
See application file for complete search history.

(56) References Cited

U.S. PATENT DOCUMENTS

| | | | | |
|---|---|---|---|---|
| 3,183,073 A | * | 5/1965 | Preston | 71/1 |
| 3,639,170 A | * | 2/1972 | Hutton et al. | 127/31 |
| 4,099,983 A | * | 7/1978 | Wittenberg | 127/63 |
| 4,172,783 A | * | 10/1979 | Adams et al. | 210/677 |
| 4,404,038 A | * | 9/1983 | Credoz et al. | 127/60 |
| 4,871,573 A | * | 10/1989 | Bohren et al. | 426/588 |
| 5,747,647 A | * | 5/1998 | Stack et al. | 530/365 |
| 5,851,372 A | * | 12/1998 | Noel | 204/523 |

FOREIGN PATENT DOCUMENTS

| | | |
|---|---|---|
| EP | 0249368 A2 | 12/1987 |
| EP | 0273485 * | 7/1988 |
| EP | 0 587 972 A1 | 3/1994 |
| GB | 2 044 771 A | 10/1980 |

OTHER PUBLICATIONS

Singh, Rakesh K. et al, "α-Lactose Monohydrate from Ultrafiltered Whey Permeate in One-step Crystallization Using Ethanol-Water Mixtures", *J. Food Sci.*, vol. 56, No. 3, 1991.
Yilmaz, Remziye and Temiz, A., "Lactose crystallization from deproteinized whey in an ethanol-water system", *Milchwissenschaft*, vol. 52, No. 11, 1997.
Brothersen et al., "Recovery of Calcium Phosphate from Ultrafiltration Permeates," Journal of Dairy Science, 65:17-23, 1982.
Hull, M.E., "Commercial Production of Lactose," Journal of Dairy Science, 41:330-331, 1958.
Parrish et al., "Demineralization of Cheddar Whey Ultrafiltrate with Thermally Regenerable Ion-Exchange Resins: Improved Yield of α-Lactose Monohydrate," Journal of Food Science, 44(2):555-557, 1979.
Lewis, Sr., Richard J., Hawley's Condensed Chemical Dictionary, 12th Ed. (1993) pp. 679-680.
Singh et al., "α-Lactose Monohydrate from Ultrafiltered Whey Permeate in One-Step Crystallization Using Ethanol-Water Mixtures," *Journal of Food Science* 56:777-781 (1991).

* cited by examiner

*Primary Examiner*—Shaojia Anna Jiang
*Assistant Examiner*—Michael C Henry
(74) *Attorney, Agent, or Firm*—DLA Piper LLP (US)

(57) ABSTRACT

The present invention relates to improved methods of purification of sugars and in particular to a method of preparing lactose. A low purity lactose source such as whey is subjected to a first demineralization step involving either ion-exchange or the addition of divalent metal cations, followed by a second demineralization step where alcohol is added. The invention also relates to lactose produced by this method and products comprising lactose produced by this method.

26 Claims, 5 Drawing Sheets

METHOD FOR PURIFICATION OF LACTOSE

CROSS-REFERENCE TO RELATED APPLICATIONS

This application claims priority under 371 to PCT Application No. PCT/AU01/01641, filed Dec. 19, 2001, which claims priority to Australian Patent Application No. PR 2177, filed Dec. 19, 2000.

TECHNICAL FIELD

The present invention relates to improved methods of purification of sugars and in particular to a method of preparing lactose, lactose produced by the method and products comprising lactose produced by the method.

BACKGROUND

Industrial process waste streams such as dairy process streams are useful sources for the manufacture of sugars, in particular the manufacture of lactose. Whey, which is a watery liquid that separates from curd when milk is clotted, as in cheese making, contains valuable nutrients, including considerable amounts of lactose. Since lactose is a commercially important product particularly in the manufacture of infant milk-substitute formulas, confectionery, chocolate, baked goods, etc, several methods have been developed for its isolation from whey. Lactose also has important applications in the pharmaceutical industry particularly in tabletting and for dry powder inhalers.

To date, most methods for the production of refined edible or pharmaceutical grade lactose from whey involve more than one crystallisation step. Precipitation of lactose, however, is a relatively slow process and re-crystallisation increases both time and costs associated with production. Crude lactose α-monohydrate with an ash of 1% has recently been extracted from deproteinised whey using a water-ethanol one step crystallisation process (Yilmaz and Temiz, 1997, Milchwissenschaft 52 (11) p 629-631). However, lactose obtained by such a method remains unsuitable for most food applications which require an ash content of <0.3% (edible grade) or <0.2% (refined edible) and for pharmaceutical applications which require an ash content of <0.1%. Singh et al (1991, J Food Sci 56 (3) p. 777-788) disclose demineralisation of whey permeate using ion exchange resins followed by alcoholic crystallisation directly from the resulting solution. Although pharmaceutical grade lactose can be obtained using this method, the disadvantage of the method is that large columns of cation and anion exchange resins are required and the lactose is crystallized at pH 2.5 in 80% ethanol with stirring for 3 h. Further, this method requires regeneration of columns and disposal of the alkaline/salty regenerant, and involves an acid wash in which hydrochloric acid is commonly used. It is well known that hydrochloric acid is corrosive to the stainless steel used in equipment, such as tanks, centrifuges, pumps, etc. in which these methods are generally performed. Consequently, it would be desirable to have an alternative simple and economical process for the production of high purity lactose from a lower purity source.

It is an object of the present invention to provide a method of crystallisation of lactose and a product thereof which will overcome or substantially ameliorate at least some of the deficiencies of the prior art or provide a useful alternative.

The inclusion in this specification of references to prior art is not to be taken as an admission that the cited prior art, or any part thereof, comprises the common general knowledge of those skilled in the field of the invention.

SUMMARY OF THE INVENTION

The present invention is based on the observation that a simple and economical process, which involves the removal of impurities such as proteins, mineral salts and riboflavin from a low purity lactose source by two demineralisation steps, can provide higher purity lactose.

According to a first aspect, the invention provides a method of preparing high purity lactose from a lower purity lactose source including two demineralisation (as herein defined) steps as follows:

(a) primary demineralisation, and
(b) secondary demineralisation of the resultant of step (a) including the addition of alcohol in an amount, for a time, and at a temperature, sufficient to precipitate minerals.

Preferably, the resultant of step (b) is crystallised by a further step (c). Preferably, the crystallisation is carried out by a single step procedure. Preferably, the crystallisation is carried out over a period of about 4 hours and more preferably over a period of about 2 hours.

Preferably, the primary demineralisation step includes treatment of the lower purity lactose source with divalent metal ions in an amount, for a time and at a temperature sufficient to remove certain mineral impurities before subjecting the lactose-containing solution to alcohol treatment. However, it will be clear to the skilled addressee that the primary demineralisation step may be achieved by passage of the lower purity lactose source through a cation exchange resin (to remove divalent cations such as calcium and magnesium) and an anion exchange resin (to remove multivalent or divalent anions such as citrate or phosphate).

Preferably, the resultant of step (a) is concentrated to 20% to 60% total solids before step (b).

Preferably, the divalent metal ion is calcium and more preferably the calcium is in the form of calcium chloride or calcium hydroxide (lime). However, it will be clear to the skilled addressee that other sources of divalent metal ions will also be useful eg. magnesium chloride or barium chloride. Preferably the divalent metal ion is present at a concentration of 0.014 to 0.025 M. The concentration will vary according to the level of precipitable divalent anions (e.g. phosphate) present in the lactose source.

Preferably, the alcohol is ethanol. However, the skilled addressee will understand that other alcohols may also be used in the invention such as methanol, isopropanol and propanol. Taking into account the boiling point and other relevant characteristics of these alcohols, the skilled addressee will be able to determine suitable and optimal conditions under which the method should be performed.

When the alcohol is ethanol, preferably, in step (b), the ethanol is present at between 25% and 75% total liquid volume. Most preferably it is present at approximately 60% total liquid volume.

Preferably, in step (b) the temperature of the divalent metal ion-treated solution and the alcohol is between 40° C. and 79° C. More preferably it is about 78° C.

Preferably, the step (c) is carried out in alcohol and preferably the alcohol is present at between 25% to 75% total liquid volume. Preferably the crystals formed in step (c) are washed with an alcoholic solution containing between 0% and 20% water.

Preferably, the lactose produced by the present invention has less than 0.3% ash. Most preferably it is pharmaceutical grade lactose with less than 0.1% ash.

If clarified whey (screened to remove cheese particles and centrifuged to remove fat) is used as a lactose source, the divalent metal ion treatment step is advantageously preceded by an ultrafiltration step to obtain whey permeate. The divalent metal ion-treated solution is optionally treated with absorbents such as charcoal, and then advantageously concentrated by nanofiltration and evaporation prior to treating with alcohol to precipitate the residual minerals.

Lactose crystals obtained by the method of the invention are optionally recovered by centrifugation, washed and dried.

According to a second aspect, the invention provides a method for the production of crystalline lactose of pharmaceutical grade from clarified whey solution including the steps of:

(a) ultrafiltration of the clarified whey solution to obtain whey permeate;

(b) primary demineralisation of the solution from step (a) by treatment with 0.014 to 0.025 M calcium chloride and/or calcium hydroxide;

(c) filtration or centrifugation of the solution from step (b) and, optionally, treatment of the solution with charcoal;

(d) concentration of the solution from step (c) to 20% to 60% total solids;

(e) secondary demineralisation by addition of ethanol to the solution from step (d) to a final concentration of about 60%;

(f) filtration or centrifugation of the solution from step (e);

(g) crystallisation of lactose from the solution from step (f);

(h) centrifugation of the solution from step (g) and removal of lactose crystals; and (i) washing lactose crystals obtained in step (h) with an alcoholic solution containing between 0% and 20% water and drying the crystals.

Preferably, the concentration of the solution from step (c) is by nanofiltration and evaporation. However, the skilled addressee will be aware that other concentration means may be employed such as reverse osmosis.

According to a third aspect there is provided an improved method for the preparation of lactose crystals of at least food grade standard from a lower purity lactose source, the improvement including the steps of:

(a) treating a solution containing lactose with divalent metal ions in an amount, and for a time, sufficient to remove a proportion of minerals contained in the solution; and (b) treating the divalent metal ion-treated solution with alcohol in an amount, and for a time, sufficient to remove residual minerals from the solution.

According to a fourth aspect, the invention provides lactose produced by a method according to any one of the first to third aspects.

Preferably, the lactose is of food grade standard. Most preferably the lactose is pharmaceutical grade lactose. Preferably, the lactose has a bulk density of 0.40 to 0.70 g/ml. Most preferably the lactose is in the form of rosette-shaped crystals.

According to a fifth aspect, the invention provides a pharmaceutical preparation comprising lactose according to the fourth aspect.

According to a sixth aspect, the present invention provides a veterinary preparation comprising lactose according to the fourth aspect.

Preferably, the preparation is in the form of a powder, tablet, capsule or caplet.

According to a sixth aspect, the invention provides a product including lactose produced by a method according to any one of the first to third aspects.

Preferably, the product is a food product. In one embodiment, the product is an infant formula or milk substitute formula.

However, it will be clear to the skilled addressee that the product may be any product in which the lactose obtained by the method of the present invention would be useful and the skilled addressee will be aware of such products. For example, in addition to the products indicated above, the product may also be an agricultural product. The free-flowing properties of the lactose crystals obtainable by the present method are particularly useful in tablet products and agricultural products in the form of tablets are specifically contemplated eg. fertilisers, insecticides, fingicides and the like.

It will be clear to the skilled addressee that by-products of the invention are also contemplated. Hence, according to a seventh aspect, the invention provides a by-product of the method of any one of the first to third aspects.

Preferably, the by-product is a calcium-rich mineral fraction.

According to an eighth aspect, the invention provides a food product including a by-product according to the seventh aspect. Preferably, the food product is a sports, diet and/or dairy food.

According to a ninth aspect, the present invention provides a drink product including a by-product according to the seventh aspect. Preferably, the drink product is a sports, diet and/or dairy drink.

In the context of the present invention, the term "demineralisation" means precipitation of impurities followed by removal of the impurities.

In the context of the present invention, the term "lower purity lactose source" encompasses sources of lactose which range from very crude sources such as products of the dairy industry eg. whey, to sources which have previously been purified by other methods including, for example, refined food grade lactose and the like. However, it does not include a source in which the lactose is solely pharmaceutical grade lactose.

In the context of the present invention, the term "high purity lactose" refers to lactose having less than 1% ash such as, for example, food grade lactose (currently <0.3% ash), refined food grade lactose (currently <0.2% ash) and pharmaceutical grade lactose (currently <0.1% ash).

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

It will be understood that the principles described above may also be applied to purification of other sugars, for example sucrose, glucose, fructose and fruit sugars.

DESCRIPTION OF THE INVENTION

Figure 1:
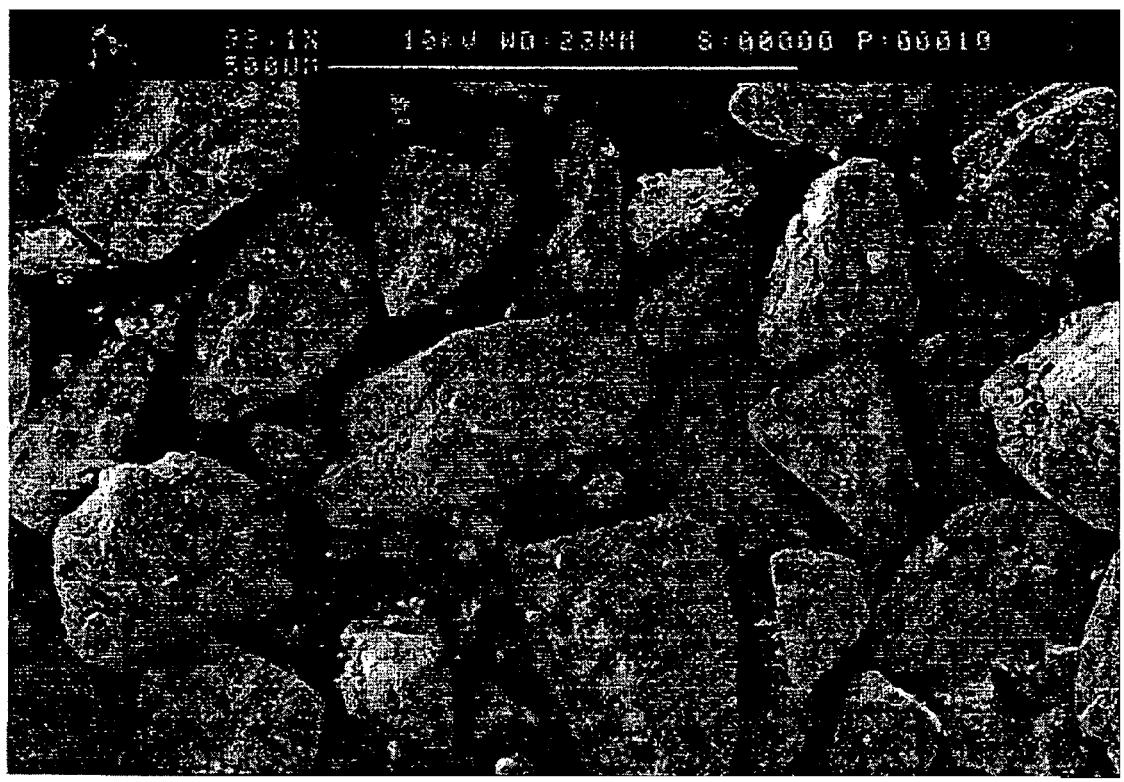
FIG. 1 Micrograph of crystals of 100 mesh Wyndale α lactose monohydrate from The Lactose Company of New Zealand, Havera, New Zealand.

A preferred embodiment of the invention will now be described, by way of example only. The method described is referred to hereinafter as the "accelerated alcoholic crystallisation" (AAC) method.

This embodiment involves the addition of calcium to the permeate from the ultrafiltration of whey to remove minerals. This addition is followed by nanofiltration and evaporation (concentration) of the calcium treated whey permeate. This addition is then followed by ethanol treatment. The minerals precipitated by the addition of ethanol are removed and the lactose crystallised, the crystals washed and dried. The steps lead to four different fractions. The main product recovered is highly pure lactose. Also recovered are a mineral fraction from the calcium treatment step, a mineral fraction from the alcoholic demineralisation step and molasses from the mother liquor. The ethanol left in the alcoholic mineral precipitate and the mother liquor can be recycled if recovered by distillation.

The different steps of the process are shown on the AAC process flow chart (Scheme 1). The calcium-treatment: adjusting the pH to 7 by addition of calcium chloride and sodium hydroxide or calcium hydroxide and then centrifuging, enables an efficient demineralisation of the whey permeate by producing a mineral fraction rich in calcium, phosphate and citrate. This fraction can be roller dried into a white powder. The calcium-treatment step can also be substituted by the use of cation and anion resins.

The whey permeate is then concentrated in two steps by nanofiltration and evaporation up to 50% total solids.

With the addition of alcohol to the lactose solution, residual minerals precipitate and are removed from solution by centrifugation or filtration, which is followed by crystallisation, washing and drying of the lactose crystals.

Example 1

Primary Demineralisation

The calcium-treatment step is the first part of the AAC process, which comprises 5 unit steps. The raw material for the AAC process can be whey coming from the manufacture of cheese. The chemical composition of cheese whey is described in table 1 with data from both the literature and experiments.

When cheese whey is used, it is first seived to remove fines, centrifuged to remove fat, pasteurized and then ultrafiltered producing 2 streams: ultrafiltration (UF) retentate and whey permeate. The UF retentate has preferably 12% solids and 5.2% lactose. The ash of this UF retentate is 0.99%+/−0.13. The whey permeate chemical composition is presented in table 2.

The next step is called primary demineralisation. It is the first critical step of the process. The whey permeate is neutralised to pH 7 by addition of Calcium Chloride and Sodium Hydroxide or Calcium Hydroxide. The whey is then heated to 60° C. and kept at this temperature for 15 minutes during which time a precipitate is formed and is subsequently removed by centrifugation or filtration.

The chemical compositions of both the calcium-treated whey permeate and the precipitate (called calcium rich mineral fraction) are described in table 3. The calcium-treated whey permeate is either pumped through a charcoal column and/or cooled to around 20° C. before being nanofiltered. The temperature of the lactose solution pumped to the nanofiltration unit depends upon the characteristics of the membranes used in the nanofilter. Usually as the temperature increases the proportion of lactose permeating through the nanofilter membrane increases. The lower temperature (=/<20° C.) is thus used to minimise the loss of lactose into the nanofiltration permeate. The charcoal column treatment is an optional step that can be done either before or after the nanofiltration.

TABLE 3

Chemical composition of calcium-treated whey permeate and calcium rich mineral fraction.

| Component | Ca-treated whey permeate | Ca-rich mineral fraction |
|---|---|---|
| | g/100 g Whey | g/100 g Precipitate |
| Dry matter | 5.3 +/− 0.6 | 25 +/− 2.4 |
| Ash | 0.91 +/− 0.2 | 9.5 +/− 0.73 |
| Lactose | 4.27 +/− 1.2 | 6.75 +/− 1.78 |
| | mg/100 g Whey | mg/100 g Precipitate |
| Citric acid | 115 +/− 16 | 1794 +/− 163 |
| Sodium | 44 +/− 8.7 | 108 +/− 60 |
| Potassium | 147 +/− 8.2 | 192 +/− 75 |
| Calcium | 107 +/− 50 | 4002 +/− 449 |
| Magnesium | 6.6 +/− 0.9 | 80 +/− 18 |
| Phosphorus | 11 +/− 1.5 | 1966 +/− 147 |
| Sulphur | 6.6 +/− 2.8 | 24 +/− 13 |

The calcium-rich mineral fraction can be dried (i.e. roller drying) to give a white to off-white powder. This powder should be useable in a number of calcium and mineral supplemented products such as sports drinks, dairy drinks, sports and diet food, chocolate and so on. This powder has to be considered not so much as a by-product but rather as a value-added product with a "natural" marketing advantage.

The nanofiltration of the calcium-treated whey permeate produces two streams of liquid products: some salty water as the permeate; and, the concentrated whey as the nanofilter retentate. The chemical composition of the nanofilter retentate is presented in table 4.

TABLE 4

Chemical composition of nanofilter retentate.

| Component | Nanofilter Retentate |
|---|---|
| | g/100 g Retentate |
| Dry matter | 19.2 +/− 1.9 |
| Ash | 1.9 +/− 0.43 |
| Lactose | 15.4 +/− 1.5 |
| | mg/100 g Retentate |
| Citric acid | 403 +/− 23 |
| Sodium | 44 +/− 17 |
| Potassium | 186 +/− 48 |
| Calcium | 353 +/− 109 |
| Magnesium | 25 +/− 3.4 |
| Phosphorus | 35 +/− 4.4 |
| Sulphur | 15 +/− 3 |

The nanofiltration step is used to not only concentrate the calcium-treated whey, but also to effectively reduce, when compared with the effect of direct evaporation, the potassium and sodium concentrations in the nanofilter retentate. The calcium-treated whey is concentrated to 20°Brix which is higher than that obtained in most other industrial scale nanofiltration processes. This concentration is readily achievable because of the smaller osmotic pressure across the nanofilter membrane due to low divalent salt concentrations in the calcium-treated whey permeate. However, the permeate is not concentrated above 20°Brix because the flux across the membrane drops rapidly at 20°Brix, making further concentration uneconomic compared to evaporation. Also the constant proportional percentage of lactose lost through the membranes used is minimised by these process conditions: −20 Bar, 20° C. maximum, 20°Brix maximum.

The last step of the calcium-treatment is to further concentrate the nanofilter retentate. A multi-effect evaporator is usually used to take the total solids from 20°Brix to between 40° and 50°Brix. The chemical composition of the concentrated nanofilter retentate (CNR) is shown on Table 5.

TABLE 5

Chemical composition of concentrated nanofilter retentate (CNR).

| Component | Concentrated nanofilter retentate |
|---|---|
| | g/100 g retentate |
| Dry matter | 41 +/− 4 |
| Ash | 3.89 +/− 0.9 |
| Lactose | 38 +/− 0.33 |
| | mg/100 g retentate |
| Citric acid | 787 +/− 18 |
| Sodium | 94.3 +/− 38 |
| Potassium | 408 +/− 90 |
| Calcium | 656 +/− 23 |
| Magnesium | 55 +/− 5 |
| Phosphorus | 70 +/− 10 |
| Sulphur | 31 +/− 9 |

Example 2

Alcohol Addition Step

The AAC process includes an alcohol treatment of the concentrated nanofilter retentate (CNR) as a further demineralisation step, followed by filtration, crystallisation, washing and drying of the crystals.

As an example, the basic unit operations for the alcohol addition stage of the AAC process, include:

(1)—Pumping 40 Kg of the CNR at a flow rate equivalent to 4 Kg/min from a storage tank, through a heat exchanger to bring the CNR from 45° C. to 78° C., and into the first stirred tank called the "demineraliser".

Pumping 30 L 100% ethanol (volume of ethanol to add is 60% of total liquid [water+ethanol]) at a flow rate equivalent to 3 L/min from a storage tank, through a heat exchanger to bring the ethanol from room temperature to 78° C., and into the demineraliser.

(2)—Demineralising the alcoholic CNR by leaving it under reflux at 78° C. and low stirring for one to 15 minutes. A condenser fitted on the lid of the demineraliser tank, condenses the alcoholic vapours which are returned to the demineraliser tank.

(3)—Filtering the alcoholic CNR solution after step (2) by pumping the mixture at an average flow rate of 2 L/min, through a 1 μm filter at 78° C. This filtration step removes the precipitated solids from the alcoholic CNR liquid phase.

Steps (1), (2) and (3) are called the "demineralisation step". It produces a precipitate recovered by filtration called "alcoholic demineralisation mineral fraction". The alcoholic demineralised CNR is then ready for the crystallisation step. Table 6 describes the chemical composition of the alcoholic demineralisation mineral fraction.

(4)—Crystallising lactose by cooling the solution in a second stirred tank called the "crystalliser" over 2 hours. Seeding the crystalliser (adding a small amount of lactose crystals of a known crystal size) is also necessary at this stage.

(5)—Separating the crop of lactose crystals from the mother liquor by centrifugation. Gravity or a pump can be used to feed the mixture containing the lactose crystals into the centrifuge. The crystals are retained in the centrifuge while the mother liquor spun-off is pumped into a waste drum. The ethanol left in the mother liquor can be recovered by distillation and recycled. The solids left in the mother liquor can be dried into a powder called "dry molasses". The chemical composition of the dried mother liquor is presented in table 7.

(6)—Washing the crop of lactose crystals. The washing solution, consisting of between 80 and 100% v/v ethanol with the remainder water, is heated to 70-75° C. by pumping through the ethanol heat exchanger. The volume of washing solution used is proportional to the amount of solids present in the concentrated whey at the start of the AAC process. From two to six liters of washing solution should be used per Kg of solids present. The washing solution can be recycled by distillation. Its chemical composition is described in table 7. Highly pure lactose crystals were also produced with a washing solution that had its pH adjusted to 2 with hydrochloric acid.

The combination of the four steps described:—calcium-treatment, ethanolic demineralisation, crystallisation and crystal washing, results in a crop of lactose crystals of very high purity which may be suitable for use in the pharmaceutical industry.

The process lactose specifications are described in table 8.

(7)—Drying the crystals under mild conditions: preferably at or below 60° C. in a fluidised bed dryer.

TABLE 6

Chemical composition of the demineralisation mineral fraction.

| Component | Alcoholic Demineralisation mineral fraction |
|---|---|
| | g/100 g Precipitate |
| Dry matter | 40 +/− 2 |
| Ash | 15 +/− 3 |
| Lactose | 16 +/− 2.5 |
| Citric acid | 4.9 +/− 1.1 |
| Sodium | 0.25 +/− 0.02 |
| Potassium | 0.92 +/− 0.08 |
| Calcium | 7.6 +/− 1 |
| Magnesium | 0.24 +/− 0.01 |
| Phosphorus | 0.37 +/− 0.05 |
| Sulphur | 0.25 +/− 0.06 |

TABLE 7

Chemical composition of the dried mother liquor and washing solution.

| Component | Dried Mother liquor | Washing Solution |
|---|---|---|
| | g/100 g Molasses | g/100 g Solution |
| Dry matter | 11 +/− 2.5 | 1.11 +/− 0.6 |
| Ash | 2.34 +/− 0.5 | 0.24 |
| Lactose | 3 +/− 1 | 0.572 |
| | mg/100 g Molasses | mg/100 g Solution |
| Citric acid | 459 +/− 30 | 60 +/− 20 |
| Sodium | 92 +/− 30 | 10 |
| Potassium | 340 +/− 54 | 37 |
| Calcium | 454 +/− 50 | 29 |
| Magnesium | 50 +/− 3 | 4.4 |
| Phosphorus | 47 +/− 20 | 5.5 |
| Sulphur | 30 +/− 10 | 2.2 |

TABLE 8

AAC lactose specifications.

| Component | AAC Lactose |
|---|---|
| Lactose | 99.8% min. |
| Water | 5% |
| Sulphated Ash | ≦0.3% |
| Loss on drying | 0.047% |
| Specific rotation | 55.9° |
| Heavy metals | <5 mg/Kg |
| Arsenic | <0.25 mg/Kg |
| Acidity ml 0.1N NaOH/6 g | 0.15 ml/6 g |
| Protein and light-absorbing impurities absorbance | 210-220 nm: 0.14 max. 270-400 nm: 0.07 max. |
| Solution appearance | clear, colourless |
| Sediment | absent/100 g |
| Total bacterial count | 100/g max |
| Yeasts and moulds | 50/g max |
| Coliforms | Negative/g |
| *Escherichia Coli* | Negative/10 g |
| Salmonella species | Negative/100 g |

Example 3

Properties of Lactose

The pharmaceutical applications study first involved the evaluation of the physico-chemical properties of 4 pharmaceutical grade lactose powders:
The AAC lactose; and
3 other commercially available products:
  Pharmatose, DMV, roller dried, high beta content, anhydrous lactose.
  USP-100 mesh alpha lactose monohydrate from Wyndale New Zealand.
  Supertab, Wyndale New Zealand, spray dried, mix of alpha lactose monohydrate and amorphous lactose.

While there are records in the literature of extensive testing of many of the commercially-available pharmaceutical grade lactoses, it was important to validate the tests on the AAC lactose by performing the same tests at the same time on the commercial products.

The physico-chemical properties that were studied were:
The particle shape of the crystals by scanning electron microscopy.
The particle size by laser diffraction (Malvern Particle Sizer).
The bulk density (mass of known volume of particles) and tap density (mass of a known volume of compacted particles).
The moisture content.
The flow properties or flowability. The flowability is the time it takes for a certain amount of lactose powder to flow through a tube of known diameter. It is expressed in grams per second. Tables 9 and 10 present the results of the 4 lactose powders physico-chemical properties study.

The usual shape of crystalline lactose is the one presented in FIG. 1, the micrograph of the USP-100 mesh Wyndale powder.

Figure 2:
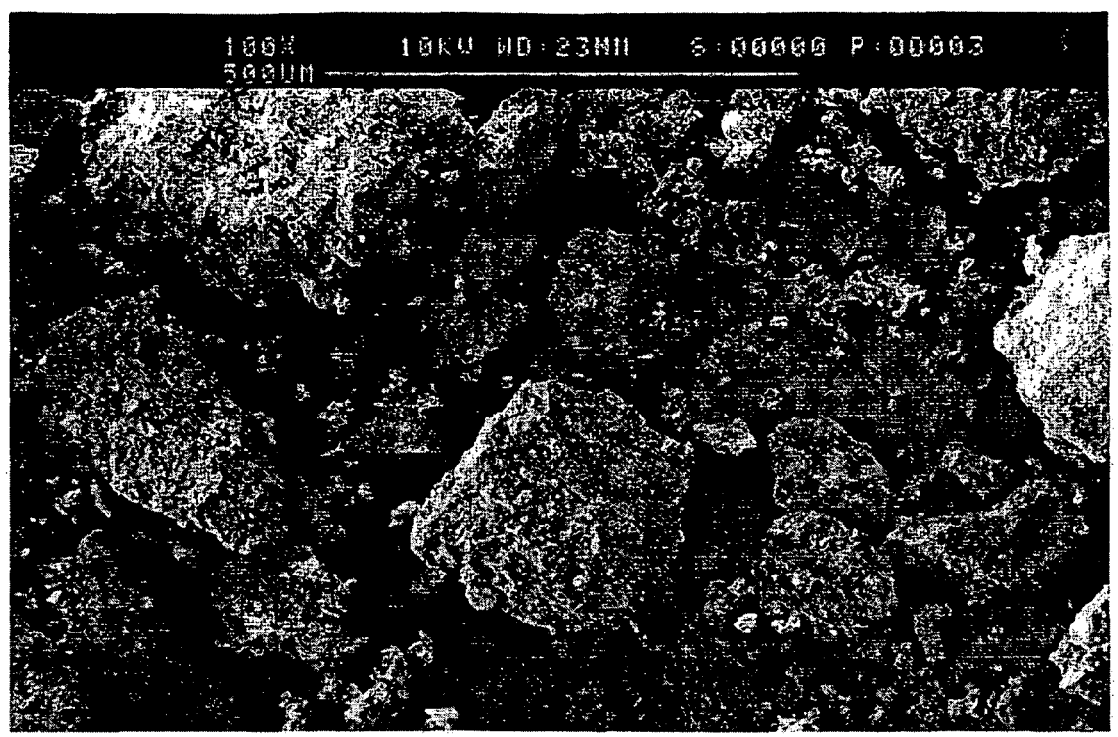
FIG. 2 Micrograph of Pharmatose: roller dried anhydrous lactose from DMV International, Veghel, The Netherlands.
Figure 3:
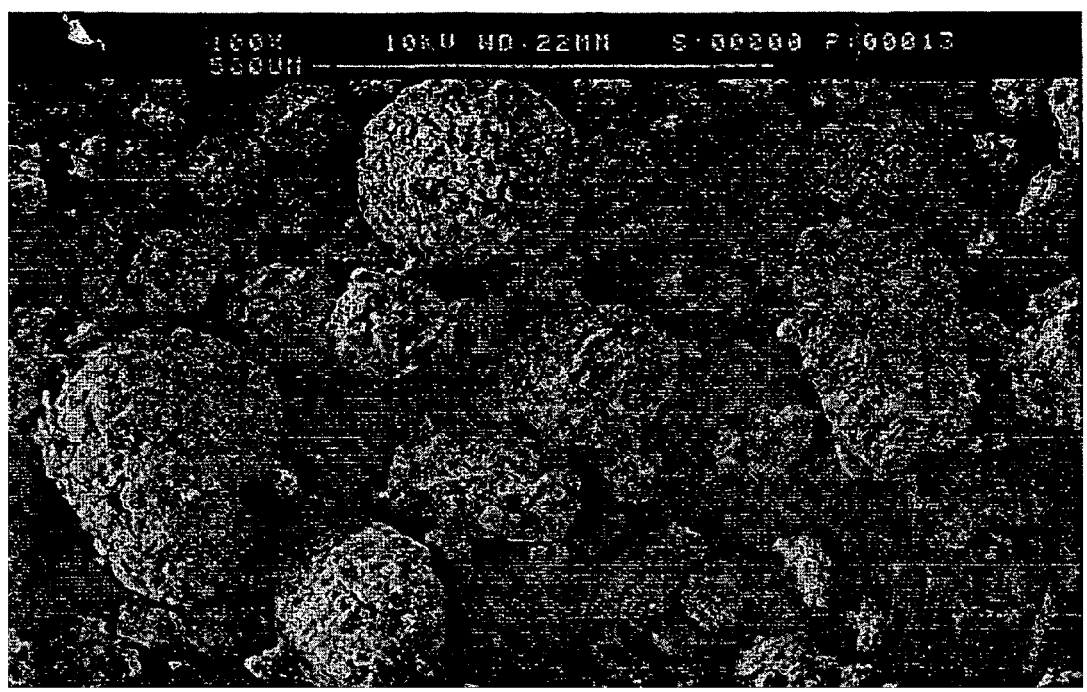
FIG. 3 Micrograph of Wyndale Supertab: spray dried lactose, a mix of α lactose monohydrate and amorphous lactose from The Lactose Company of New Zealand, Havera, New Zealand.

FIGS. 2 and 3 respectively present micrographs of Supertab spray dried lactose that has a spherical shape and Pharmatose roller dried lactose that has very irregular shape.

Figure 4:
FIG. 4 Micrograph of lactose crystals of the present invention.
Figure 5:
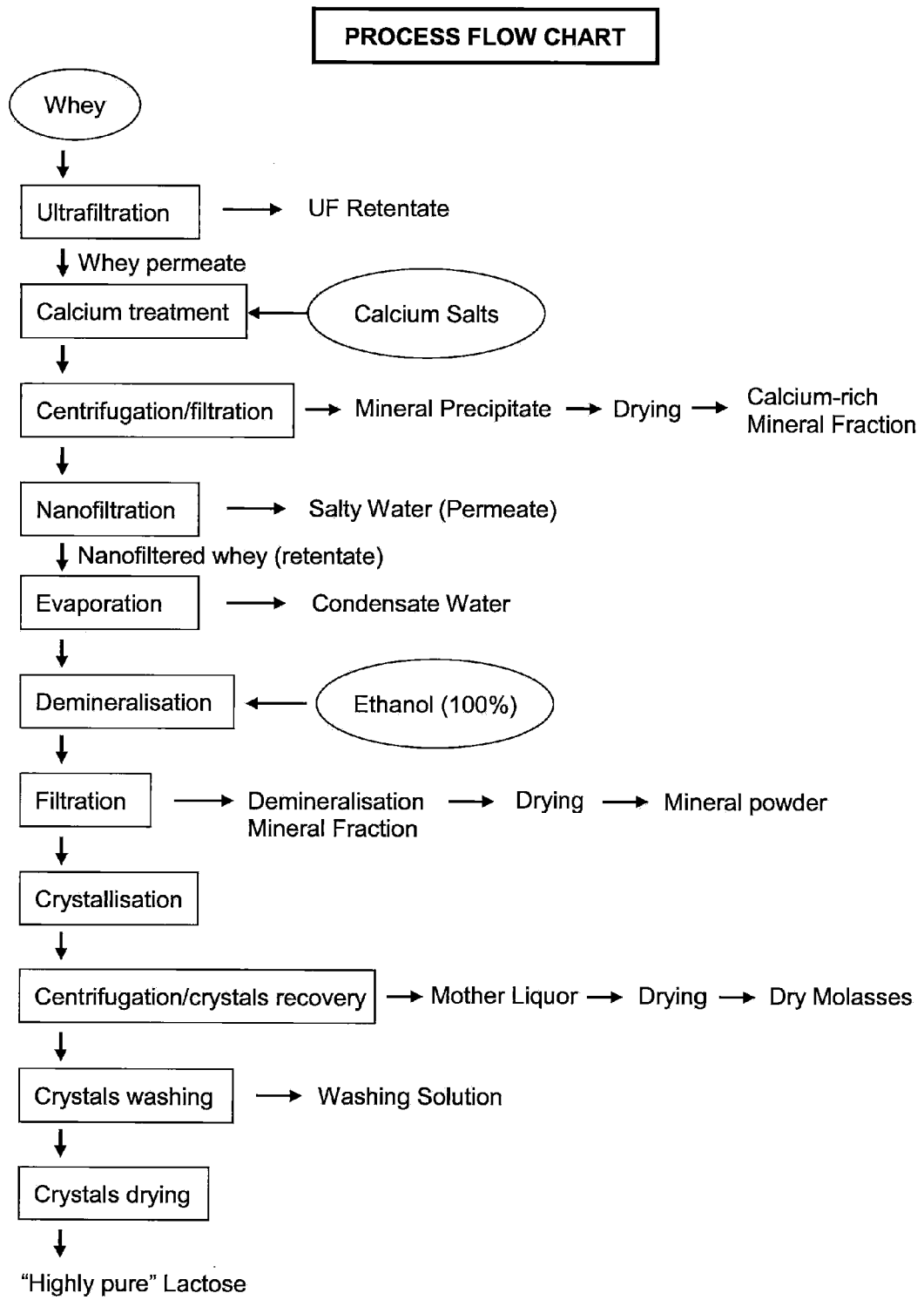
FIG. 5 Process Flow Chart

The AAC crystals have a shape which we have called "rosette" (FIG. 4). One crystal is made of a number of small microcrystals aggregated together. The AAC crystals can have a higher surface to mass ratio than commercially available lactose. This is also reflected by their higher bulk density (see table 10).

The method used to study the particle size was the Malvern Particle Sizer. It works on the principle of laser diffraction. The light source is a Helium-Neon laser. Particles are introduced into the beam; the light is scattered and then collected by a receiver lens. A detector operates in the form of a series of 31 concentric annular rings. Data is collected into a computer for further processing and printing.

TABLE 9

Particle size distribution.

| | Particle Size Distribution (microns) | | | |
|---|---|---|---|---|
| Lactose Powder | 10% under | 50% under | 90% under | Mean Particle Size |
| AAC 1 - pharmaceutical grade | 68 | 162 | 261 | 163 |
| AAC 2 - refined edible grade | 40 | 119 | 189 | 116 |
| AAC 3 - refined edible grade | 46 | 133 | 262 | 151 |
| Pharmatose - DMV | 22 | 150 | 250 | 150 |
| USP-100 mesh - Wyndale | 37 | 112 | 250 | 100 |
| Supertab - Wyndale | 47 | 145 | 250 | 150 |

TABLE 10

AAC lactose tap density, bulk density, moisture content and flowability. Comparison with some commercially available lactose powders.

| Material | Tap density g/cm³ | Bulk density g/ml | Moisture g/100 g | Flowability g/s |
|---|---|---|---|---|
| AAC 1 | 0.56 | 0.53 | 5.400 | 4.6 |
| AAC 2 | 0.54 | 0.43 | 5.020 | 3.7 |
| AAC 3 | 0.54 | 0.45 | 5.335 | 4 |
| Pharmatose | — | 0.65 | 0.220 | 0 |
| USP-100 mesh | 0.96 | 0.82 | 4.730 | 5.2 |
| Supertab | 0.77 | 0.64 | 5.180 | 4 |

Bulk density measurements made with a 100+/−0.375 ml glass cylinder; means of 6 measurements.

Tap density measurements made with a 477.2 cm³ cylinder; means of 6 measurements.

Moisture content: used an IR moisture determination balance MA 30, 140° C., 7 min; means of 2 measurements.

Flowability measurements made using a static funnel, a tube a known diameter (8 mm) and a balance; means of 5 measurements.

Example 4

Tabletting Trials

There are 3 different ways to make tablets: dry granulation, wet granulation and direct compression. In the granulation processes, the drug, the excipient and other additives are mixed and then granulated. Granulation improves the flow properties. If the flow properties are poor, this will lead to variations in the fill of the tablet die and will result in weight variation and therefore in dose variation. Once the mix is free flowing, it is compressed in a tabletting machine. Some powder is pushed into the tablet die, then compressed by a puncher and finally the tablet ejected from the die.

The direct compression technique was developed in the sixties when spray dried lactose appeared on the market. Spray dried lactose had relatively good flow properties and it also had excellent binding properties hence it could be compressed without granulation.

Avoiding the granulation steps saves a lot of time but on the other hand, the quality of the excipient has to be higher with good flow and good binding properties and also good storage stability. The excipient should also allow the drug to be made available at the right time. The mixing step is critical in direct compression because this is the only way to make sure the drug dose will be the same for all the tablets. For the 3 lactose powders we had to compare, we applied the same conditions of formulation, mixing, processing and testing. The tabletting machine used was a Manesty type F8. Once the tablets were made, 5 tests were performed to assess the tablet quality.

The first test was the number of tablets produced per kilo of lactose and the yield. AAC lactose gave 1152 tablets with a yield of 60%. This means the production was 60% of the tablets we could theoretically have made. Pharmatose gave 1038 tablets with a yield of 54%. Supertab gave 891 tablets with a yield of 46%. The better result of AAC lactose comes from the fact it has bigger crystals and less fines. Less lactose is lost either as dust or as powder escaping the machine die.

The second test was hardness. The number indicates if the tablet is soft or strong and reflects the binding properties of the excipient. A good hardness is usually around 5-6 KPa. AAC lactose was 5.7 KPa, Pharmatose was 5.7 and Supertab 4.7 KPa There was not much difference for this parameter. The test was performed with a Schleuniger tester.

The friability test indicates the ability to withstand aggressive handling. The tablets are going to be carried along the processing line to be packaged then transported and stored.

Friability gives the percentage of material lost during handling. The smaller the value the better. AAC lactose performed well with only 0.43% friability against 0.51% for Pharmatose and 1.95% for Supertab. The test was performed on a Erweka-Apparatebau machine.

Disintegration time is the time it takes to a tablet to disintegrate under mechanical and chemical actions. This test shows how long the tablet takes to break up (but not to dissolve as opposed to the solubility test) and demonstrate the ability of the tablet to release the drug quickly. Disintegration time depends on the excipient properties. AAC lactose tablets disintegrate the fastest. The drug will be able to dissolve in the stomach media as soon as the tablets are disintegrated and release the drug.

The dissolution test shows how fast the drug will dissolve in the stomach to be available for absorption. According to the British Pharmacopoeia, 70% of the drug has to dissolve in 0.1M HCl at 37° C. (to mimic the stomach conditions) within 45 minutes. The drug we used in the trials was caffeine as it was readily available to us. 94.5% of the caffeine was dissolved after 45 minutes in the AAC tablets against only 73% for Pharmatose and 77.5% for Supertab.

These tabletting trials showed that AAC lactose could be an excellent excipient in direct compression but its properties make it also useful in a wider range of applications. AAC lactose has a "rosette" particle shape, ideal particle size distribution without hammer milling, excellent flow properties, good compressibility, low friability, fast disintegration and high drug release.

Although the invention has been described with reference to specific examples, it will be appreciated by those skilled in the art that the invention may be embodied in many other forms.

The claims defining the invention are as follows:

1. A method for the production of crystalline lactose of pharmaceutical grade from clarified whey solution including the steps of:
   (a) ultrafiltration of the clarified whey solution to obtain whey permeate;
   (b) primary demineralisation of the solution from step (a) by treatment with about 0.014 to 0.025 M calcium chloride and/or calcium hydroxide;
   (c) filtration or centrifugation of the solution from step (b) and, optionally, treatment of the solution with charcoal;
   (d) concentration of the solution from step (c) to 20% to 60% total solids;
   (e) secondary demineralisation by addition of ethanol to the solution from step (d) to a final concentration of about 60%;
   (f) filtration or centrifugation of the solution from step (e);
   (g) crystallisation of lactose from the solution from step (f);
   (h) centrifugation of the solution from step (g) and removal of lactose crystals; and
   (i) washing lactose crystals obtained in step (h) with an alcoholic solution containing between 0% and 20% water and drying the crystals.

2. The method according to claim 1, wherein the concentration of the solution from step (c) is by nanofiltration and evaporation, or reverse osmosis.

3. An improved method for the preparation of lactose crystals of at least food grade standard from a lower purity lactose source, the improvement including the steps of:
   (a) treating a solution containing lactose with about 0.014M to 0.025M divalent metal ions to remove a proportion of minerals contained in the solution; and
   (b) treating the divalent metal ion-treated solution with alcohol at a concentration of about 25% to 75% total liquid volume to remove residual minerals from the solution.

4. A method of preparing high purity lactose from a lower purity lactose source including two demineralisation steps as follows:
   (a) primary demineralisation by treatment with about 0.014M to 0.025M divalent metal ions to provide a lactose-containing solution and a mineral precipitate, and
   (b) secondary demineralisation of the lactose-containing solution from step (a) including the addition of alcohol at a concentration of about 25% to 75% total liquid volume to precipitate further minerals from the solution.

5. The method according to claim 4, wherein after step (b) lactose is crystallized from the solution by a crystallisation step, step (c).

6. The method according to claim 5, wherein the crystallisation is carried out by a single step procedure.

7. The method according to claim 5, wherein the crystallisation is carried out over a period of about 4 hours.

8. The method according to claim 5, wherein the crystallisation is carried out over a period of about 2 hours.

9. The method according to claim 4, wherein the lactose-containing solution from step (a) is concentrated to 20% to 60% total solids before step (b).

10. The method according to claim 4, wherein the divalent metal ion is calcium, magnesium or barium.

11. The method according to claim 4, wherein the divalent metal ion is calcium derived from calcium chloride or calcium hydroxide; magnesium derived from magnesium chloride; or barium derived from barium chloride.

12. The method according to claim 4, wherein the alcohol is ethanol, methanol, isopropanol or propanol.

13. The method according to claim 12, wherein the alcohol is ethanol.

14. The method according to claim 13, wherein the ethanol is present at approximately 60% total liquid volume.

15. The method according to claim 4, wherein the temperature of the divalent metal ion-treated solution and the alcohol is between 40° C. and 79° C.

16. The method according to claim 4, wherein the temperature of the divalent metal ion-treated solution and the alcohol is about 78° C.

17. The method according to claim 5, wherein the step (c) is carried out in alcohol.

18. The method according to claim 5, wherein the step (c) is carried out in alcohol present at between 25% to 75% total liquid volume.

19. The method according to claim 5, wherein the crystals formed in step (c) are washed with an alcohol solution containing between 0% and 20% water.

20. The method according to claim 4, wherein the high purity lactose has less than 0.3% ash.

21. The method according to claim 4, wherein the high purity lactose is pharmaceutical grade lactose with less than 0.1% ash.

22. The method according to claim 4, wherein when clarified whey screened to remove cheese particles and centrifuged to remove fat is used as a lactose source, the divalent metal ion treatment of step (a) is preceded by an ultrafiltration step to obtain whey permeate.

23. The method according to claim 4, wherein the divalent metal ion-treated solution from step (a) is treated with one or more absorbents.

24. The method according to claim 23, wherein the absorbent is charcoal.

25. The method according to claim 23, wherein the solution treated with one or more absorbents is concentrated by nanofiltration and evaporation prior to step (b).

26. The method according to claim 4, wherein the high purity lactose is recovered by centrifugation and is further washed and dried.

* * * * *